United States Patent
Wu

(10) Patent No.: US 9,029,347 B2
(45) Date of Patent: *May 12, 2015

(54) METHOD AND MIXTURE FOR TREATING AND PREVENTING INFLAMMATORY BOWEL DISEASE

(71) Applicant: Holy Stone Healthcare Co., Ltd., Taipei (TW)

(72) Inventor: Tsung-Chung Wu, New Taipei (TW)

(73) Assignee: Holy Stone Healthcare Co., Ltd., Taipei (TW)

( * ) Notice: Subject to any disclaimer, the term of this patent is extended or adjusted under 35 U.S.C. 154(b) by 176 days.

This patent is subject to a terminal disclaimer.

(21) Appl. No.: 13/685,057

(22) Filed: Nov. 26, 2012

(65) Prior Publication Data

US 2013/0085118 A1      Apr. 4, 2013

Related U.S. Application Data

(63) Continuation-in-part of application No. 12/851,031, filed on Aug. 5, 2010, now Pat. No. 8,575,130.

(51) Int. Cl.
*A61K 31/728* (2006.01)
*A61K 45/06* (2006.01)

(52) U.S. Cl.
CPC ............... *A61K 31/728* (2013.01); *A61K 45/06* (2013.01)

(58) Field of Classification Search
None
See application file for complete search history.

(56) References Cited

U.S. PATENT DOCUMENTS

| 5,888,986 A | 3/1999 | Morales et al. |
| 7,354,910 B2 | 4/2008 | Kono |
| 2005/0080037 A1 | 4/2005 | Petrella |

FOREIGN PATENT DOCUMENTS

| BE | 904547 | 10/1986 |
| HU | 203372 | 7/1991 |
| WO | WO87/05517 | 9/1987 |

OTHER PUBLICATIONS

Healia, "Irritable Bowel Syndrome (IBS) Guide," Healia, http://www.healia.com/healthguide/guides/irritable-bowel-syndrome-ibs, Jan. 12, 2009.
Worden, Irritable bowel syndrome (IBS), Netdoctor, http://www.netdoctor.co.uk/diseases/facts/irritablecolon.htm.
WebMD, Ulcerative Colitis Prevention, WebMD, http://www.webmd.com/ibd.chrons-disease/ulcerative-colitis/ulcerative-colitis-prevention, Oct. 7, 2010.
The New York Times, Enteritis Overview, The New York Times, http://health.nytimes.com/health/guides/disease/enteritis/overview.html?print=1, Jan. 2011.
The University of Maryland Medical Center website, Chron's disease, http://www.umm.edu/altmed/articles/chrons-disease-000043.htm, 2011.
Gomis et al., Arthritis & Rheumatism vol. 50, No. 1, Jan. 2004, pp. 314-326.
Definition of prevent, WordNet Search, downloaded from the internet Dec. 15, 2008.

*Primary Examiner* — Layla Bland
(74) *Attorney, Agent, or Firm* — Muncy, Geissler, Olds & Lowe, P.C.

(57) ABSTRACT

A method and a mixture for treating and preventing the inflammatory bowel disease (IBD) by applying a predetermined therapeutically effective amount of a mixture of hyaluronic acid to individuals is disclosed. The mixture includes at least two different average molecular weight hyaluronic acids (Mw) with different rheology to gain a hyaluronic acid with the proper adhesion property, functions of tissue scaffold and insulation and treatment time, in order to treat and to prevent IBD (inflammatory bowel disease) includes ulcerative colitis, Crohn's disease or wound healing in stomach and intestine, thus to achieve the prompt treatment and to prolong the effect.

7 Claims, 6 Drawing Sheets

METHOD AND MIXTURE FOR TREATING AND PREVENTING INFLAMMATORY BOWEL DISEASE

This application is a Continuation-In-Part of application Ser. No. 12/851,031, filed on Aug. 5, 2010, now pending. The patent application identified above is incorporated here by reference in its entirety to provide continuity of disclosure.

BACKGROUND OF THE INVENTION

1. Field of the Invention

The present invention provides a method and a mixture for treating and preventing the inflammatory bowel disease (IBD) by applying a predetermined therapeutically effective amount of a mixture of hyaluronic acid to individuals. The mixture comprises at least two different average molecular weight hyaluronic acids with different rheology to gain a hyaluronic acid with the proper adhesion property, functions of tissue scaffold and insulation and treatment time, in order to treat and to prevent IBD (inflammatory bowel disease) includes ulcerative colitis, Crohn's disease or wound healing in stomach and intestine, thus to achieve the prompt treatment and to prolong the effect.

2. Description of Related Art

Hyaluronic acid also known as hyaluronan, hyaluronate and sodium hyaluronate, and generally referred to as HA, which is a natural glycosaminoglycan including the alternative N-acetyl-D-glucosamine and D-glucuronic acid moiety.

The macromolecule of hyaluronic acid in sodium salt form generally is the known composition existing for over fifty years. Referring to Meyer and et al (J. Biol. Chem. 107,629 (1934)), the hyaluronic acid intrinsically contains the high-viscosity glycosamine alternative with $\beta$ 1-3 glycuronic acid and $\beta$ 1-4 glycosamine, and the Mw of the high-viscosity glycosamine is between 50,000 Dalton (Da) and few million Dalton.

We can find the hyaluronic acid in the soft connective tissue in the body of mammals, and the skin, the vitreous humor of the eye, the synovial fluid, the umbilical cord and cartilage tissue contains higher volume of the hyaluronic acid.

The hyaluronic acid is the fluid with the elasticity, filling between the cells and the collagenous fibers and covering onto some epidermal tissues, majorly for the protection and the lubricant to cells for providing a platform for transporting the regulatory T cell to stabilize and to protect collagen network from the mechanical damage. The hyaluronic acid can be the lubricant in the tendon and the tendon sheath and on the surface of the synovial membrane due to the lubricant feature and the high shock absorber, and it is helpful for the tissue rheological mechanics, motion and the cell proliferation (referring to Delpech, B., Girard, N., Bertrand, P., Courel, M.-N., Chauzy, C., Delpech, A., 1997. Hyaluronan: fundamental principles and applications in cancer. J. Intern. Med. 242, 41-48, Rooney, P., Kumar, S., Ponting, J., Wang, M., 1995. The role of hyaluronan in tumour neovascularization. Int. J. Cancer 60, 632-36, Entwistle J, Hall C L, Turley EA Receptors: regulators of signaling to the cytoskeleton. J Cell Biochem 1996; 61: 569-77), and participating the receptor interaction on the surface of some cells; especially the major receptor of CD44. The regulatory effect of CD44 is widely accepted as a mark of the activated lymphocyte (referring to Teder P, Vandivier R W, Jiang D, Liang J, Crohn L, Pure E, Henson P M, Noble P W. Resolution of lung inflammation by CD44. Science 2002; 296: 155-158, Sheehan K M, DeLott L B, Day S M, DeHeer D H, Hyalgan has a dose-dependent differential effect on macrophage proliferation and cell death. J Orthop Res 2003; 21: 744-51).

The hyaluronic acid has the ability of creating and filling due to the organization and modification of the extracellular matrix, and is widely applied in filling the soft tissue for restraining the skin aging caused by age and light, as well as to adjust the obstacle of lipid metabolism on face, to prevent the increasing of secondary scar or scar formation on the skin.

Furthermore, the hyaluronic acid can be applied as the adjuvant agent for the eye operation or to reduce the pain while moving the knee and joint of the osteoarthritis patients.

Recently, the hyaluronic acid is applied in clinical treatment in the sodium salt form majorly in eye, skin, surgeon, artery treatment and in cosmetic fields. The hyaluronic acid with alkali metal ion, alkaline earth metal ion (for example the magnesium ion), aluminum ion, ammonium ion, and salt form of the replacement of the ammonium ion can be the carrier for assisting drug absorption (referring to Belgium Patent 904,547). The silver salt is used as the mycocide and the gold salt is used for treating the rheumatoid arthritis among the heavy metal salt of the hyaluronic acid (referring to WO 87/05517 of World Intellectual Property Organization).

The effect of treating the hipsore and the decubitus by the composition (complex) of the hyaluronic acid and the metal ion in the fourth group of periodic table, for example the zinc hyaluronate and the cobalt salt have been proven in the Hungary Patent 203,372 to the world.

Bioniche, the Canadian company, disclosed a method and related structure for using the hyaluronic acid with an effective concentration to treat cystitis in U.S. Pat. No. 5,888,986, wherein the Mw of the hyaluronic acid is more than 200,000 Da.

There is only the hyaluronic acid with the certain Mw been applied in the embodiment thereof, for example, to use the hyaluronic acid with the 650 kDa or 1,900 kDa Mw to treat the cystitis; however, the single molecular weight of the hyaluronic acid can not be used for both prompt treatment and sustained effect.

The US patent application 2005/0080037 (A1) belonging to Robert Peter Petrella, a Canadian, disclosed the use of hyaluronic acid for treating acute and over sprain and the reaction thereof, wherein the Mw of the hyaluronic acid is only between 90 thousand Da to 120 Da, and a single molecular weight of the hyaluronic acid cannot perform both prompt healing and prolonged action.

Seikagaku Kogyo, a Japanese company, has filed a U.S. Pat. No. 7,354,910 on Apr. 4, 2008 entitled "Use of Agent for treating inflammatory bowel disease" to disclose that the hyaluronic acid and hyaluronate with Mw between 600 kDa and 1,200 kDa can be applied to treat IBD. However, the degradation is too fast to retain the treating effect after injecting into the patient, therefore, it's very inconvenient for patients clinically.

SUMMARY OF THE INVENTION

The present invention has been accomplished under the circumstances in view. An object of the present invention is to provide a method a mixture for treating and preventing the inflammatory bowel disease (IBD) comprising administering to the subject a therapeutically effective amount of a hyaluronic acid mixture. The invention uses the biological activity of at least two average molecular weight (Mw) hyaluronic acids in the pharmaceutically acceptable salt with different molecular weights to treat IBD (inflammatory bowel disease). Because the low average molecular weight hyaluronic acid (LMWHA) and the high average molecular weight hyaluronic acid (HMWHA) have different adhesive, insulated and degradation rate, the hyaluronic acid with average Mw within the range of 5 kilo~1.5 million Da is categorized as LMWHA, and that between 1.5 million and 5 million Da is categorized as HMWHA. Thus, mixture of LMWHA and HMWHA can form a desired formulation, wherein the LMWHA can rapidly cover the inflammatory surface to treat IBD (for example, ulcerative colitis, acute enteritis, chronic enteritis, Crohn's disease or the wound healing in the stomach and intestine), and the HMWHA can prolong the degradation in order to achieve a longer effective period. Thus, a faster treatment and a sustained release effect may be achieved.

The average molecular weight of the hyaluronic acid of the high molecular weight hyaluronic acid (HMWHA) applied in the present invention is preferably between 1.5 million and 3.5 million Da, and more preferably 2 million Da. The average molecular weight of the hyaluronic acid of the low molecular weight hyaluronic acid (LMWHA) applied in the present invention is between 5 kilo and 1.5 million Da, preferably 1 million Da, and more preferably 0.35 million Da.

Another object of the present invention is to provide a method for treating and preventing the inflammatory bowel disease (IBD) comprising administering to the subject a therapeutically effective amount of a hyaluronic acid mixture, wherein the hyaluronic acid mixture comprises both LMWHA and HMWHA together with a steroid, immunosuppressive agent or anti-inflammatory drug in order to potentiate the effect.

Another object of the present invention is to provide a method for treating and preventing the inflammatory bowel disease (IBD) comprising administering to the subject a therapeutically effective amount of a hyaluronic acid mixture, wherein the hyaluronic acid mixture comprises both LMWHA and HMWHA forming the major active ingredient with the proper excipient (for example but not limited to gelatin, collagen, chitosan, chondroitin, carbopol, agar, carboxymethyl cellulose (CMC) or phosphate buffered saline (PBS), at least one of the foresaid item or the compound of the foresaid items) preparation to formulate as tablet (ex: enteric coated tablet), suppository (rectum suppository), foam, perfusate fluid or enema (for rectum or colon). The foresaid pharmaceutical preparation is accomplished by the common art in the field.

Another object of the present invention is to provide a method for treating and preventing the inflammatory bowel disease (IBD) comprising administering to the subject a therapeutically effective amount of a hyaluronic acid mixture, wherein the hyaluronic acid mixture comprises both LMWHA and HMWHA or the pharmaceutically acceptable salt thereof in a range from 0.5 mg/ml to 50 mg/ml, and preferable concentration is between 0.5 mg/ml to 5 mg/ml; a concentration in the solution form is in a range from 0.05% to 5% (w/v) and the preferable concentration is between 0.05% (w/v) to 0.5% (w/v).

The preferred dosage of the oral treat or prevention drug in the present invention is at least 10 to 1000 mg per administration, and the more preferred dosage is 10 to 500 mg per administration.

DETAIL DESCRIPTION OF THE INVENTION

Figure 1:
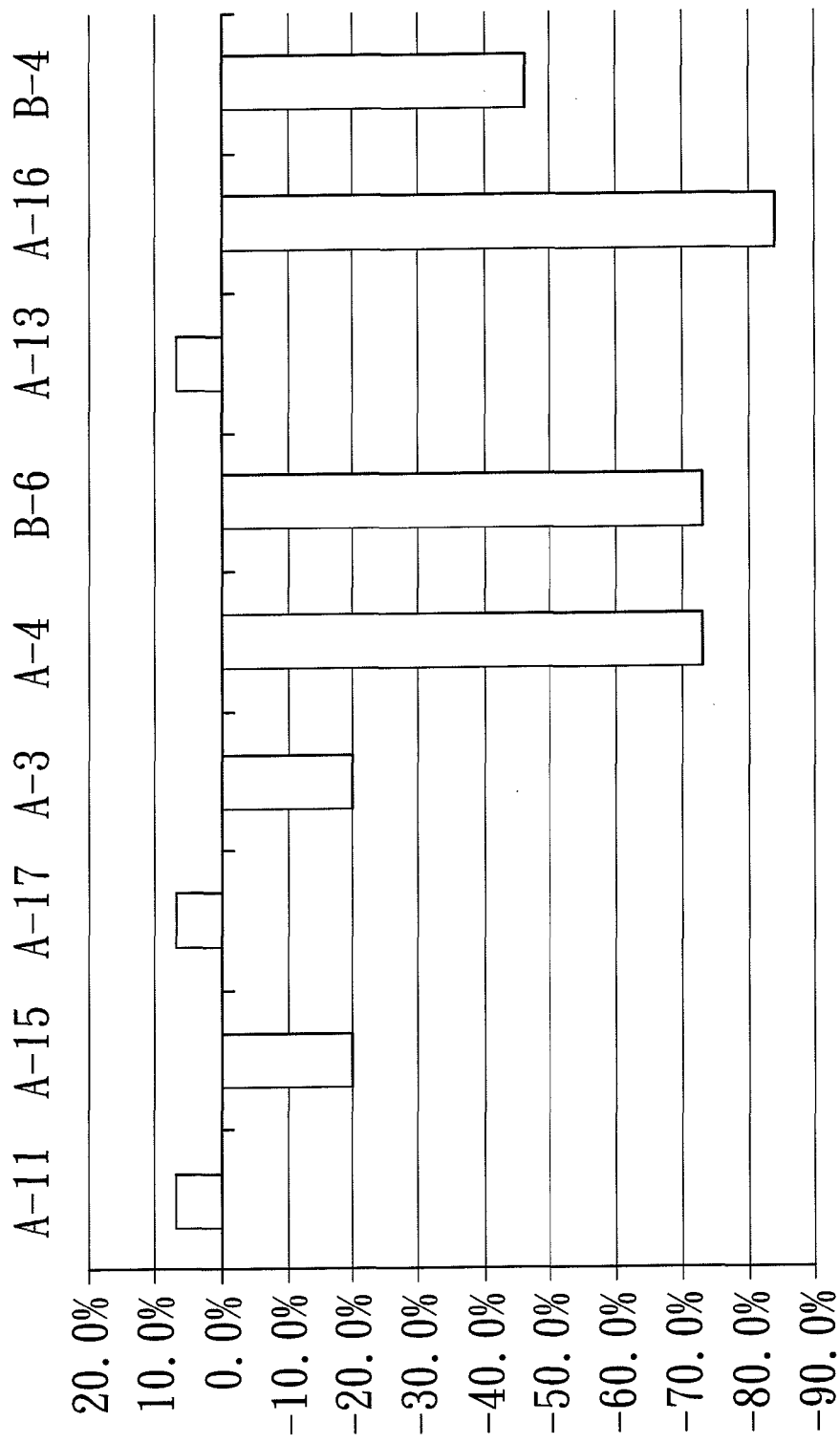
FIG. 1 illustrates a recovery (%) of the colonial lesion in mice of the treating group comparing with the control group in Example 2 in accordance with the present invention.

The invention provide a method and a mixture for treating and preventing the inflammatory bowel disease (IBD) comprising administering to the subject a therapeutically effective amount of a hyaluronic acid mixture. The hyaluronic acid mixture of the present invention used to treat and to prevent the IBD comprises at least two average molecular weight hyaluronic acids including mixture of low average molecular weight hyaluronic acid (LMWHA) and high average molecular weight hyaluronic acid (HMWHA), wherein when more than two average molecular weight hyaluronic acids are used, the third and more than third average molecular weight hyaluronic acids can be selected from low average molecular weight hyaluronic acid (LMWHA) or high average molecular weight hyaluronic acid (HMWHA). The HMWHA and the LMWHA can be a linear HA, a cross linked HA or a combination of at least one of the foresaid compounds. Different Mw has different rheology, functions of tissue scaffold and insulated and degradation in the solution, and therefore, the hyaluronic acid mixture has better adhesives and insulation and the tissue scaffold functions to balance the therapeutic effect and the degradation rate in order to treat and to prevent IBD (for example, ulcerative colitis, acute colitis, chronic colitis, Crohn's disease or to heal the wounds of the stomach and the intestines), as well as to achieve a proper treatment effect and a prolonged treatment effect. To prevent IBD is to prevent the occurrence of IBD, reduce the probability of occurrence of IBD or prevent IBD progression, which is also means amelioration of IBD.

The term "prevention" of the invention herein means a procedure, measure, substance, or program designed to prevent a disease from occurring, or a mild disorder from becoming more severe, or arrest progress of the disease and its reduce consequence once established.

The example like that aspirin provided primary prevention cardiovascular disease by conclusively reducing the risk of a first myocardial infarction (MI) by about one-third and secondary prevention by conclusively reducing risks of subsequent MI by about one-third that was written by Hennekens et al. in the second paragraph of column 2 on page 2752 of Vol. 27, No. II of Diabetes Care published in November 2004.

Inflammatory bowel disease is a chronic disease (lasting a long time), so the patient will go through periods in which the disease flares up and causes symptoms. These periods are followed by remission, in which symptoms disappear or decrease and good health returns.

Symptoms may range from mild to severe and generally depend upon the part of the intestinal tract involved. Inflammatory bowel disease generally accompanies various specific symptoms such as diarrhea, weight loss, bowel tissues edema, cell infiltration, surviving period shortening, and the like.

Intestinal complications of inflammatory bowel disease include the following: profuse bleeding from the ulcers and perforation (rupture) of the bowel Furthermore, the preventing or ameliorating mixture of the invention can be administered in order to prevent or ameliorate the above symptoms accompanied by inflammatory bowel diseases of animals. Examples of the "prevention or improvement of symptoms accompanied by inflammatory bowel diseases" include prevention or improvement of diarrhea, prevention or improvement of weight loss, inhibition of bowel tissue edema, inhibition of cell infiltration, inhibition of surviving period shortening, and the like, and as a result, a preventing or improving agent for diarrhea, a preventing or improving agent for weight loss, an inhibitor for bowel tissues edema, an inhibitor for cell infiltration, an inhibitor for surviving period shortening, and the like.

Gomis et al. (Arthritis & Rheumatism page 324 left column line 23-25, Vol. 50, No. 1, January 2004) disclosed "it is the average molecular weight and the concentration that determine the elastic and viscous properties of solution of polymers like HA". Thus, the aforesaid low average molecular weight hyaluronic acid (LMWHA) or high average molecular weight hyaluronic acid (HMWHA) are composed of hyaluronic acids of molecular weight within a predetermined range, and therefore it is to be determined by the average molecular weight, rather than by a particular molecular weight.

The quantity and specification of HA is not only being shown as molecular weight (Mw) but also as intrinsic viscosity ($\eta$) which is directly related to the Mw of a polymer through the Mark-Houwink-Sakurada (MHS) equation: $[\eta]=Km_\alpha$. For hyaluronic acid, K is 0.00057 and the exponent $\alpha$ is 0.75 at the following conditions: 0.15 M NaCl in phosphate buffer, pH 7.5, 20° C. ("Standard Guide for Characterization and Testing of Hyaluronan as Starting Materials Intended for Use in Biomedical and Tissue Engineered Medical Product Applications", ASTM Designation: F 2347-03), which is also shown in U.S. Pharmacopeial Convention, European Pharmacopeia, and Japan Pharmacopeia. When HA is represented by intrinsic viscosity, a value means an average molecular weight HA. As long as intrinsic viscosity is specified, the physical property (in other words "total function") of the intrinsic viscosity of HA is also affirmed. Both representations are acknowledged by a skilled artisan in the art, without prejudice.

The average molecular weight (Mw) lower than 1.5 million Da is categorized as low molecular weight hyaluronic acid (LMWHA), and preferably within a range between 5 kilo Da to 1.5 million Da, 10 kilo Da to 1 million Da, or 0.5 million Da to 1.5 million Da; more preferably within a range between 350 kilo Da to 1 million Da; best preferably within a range between 100 kilo Da to 750 kilo Da. The average Mw higher than 1.5 million Da is categorized as high molecular weight hyaluronic acid (HMWHA), and preferably within a range between 1.5 million Da to 5 million Da or 1.5 million Da to 3.5 million Da; more preferably within a range between 1.5 million Da to 2.5 million Da; best preferably within a range between 1.5 million Da to 2 million Da. The formulation containing a mixture of LMWHA and HMWHA, wherein the LMWHA promptly covers the inflammatory portion to treat and to prevent IBD, and the HMWHA extends the treatment effect. Thus, achieve prompt treatment and sustained release effect.

The average molecular weight of the hyaluronic acid of HMWHA applied in the present invention is also preferably 2 million Da. The average molecular weight of the hyaluronic acid of LMWHA applied in the present invention is also preferably 1 million Da.

The general chemical structure of the hyaluronan may be illustrated as follows.

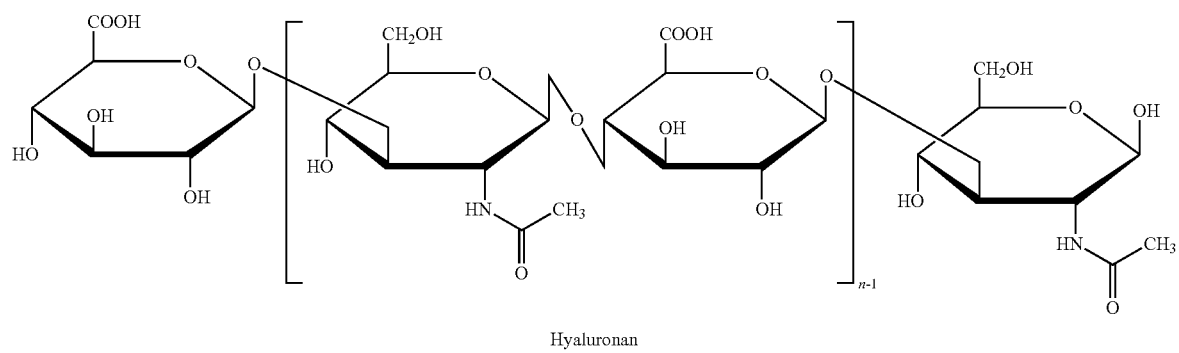

Hyaluronan

Another preferred embodiment of the present invention includes a mixture 1:1 by weight of LMWHA and HMWHA of the hyaluronic acid, and the ratio or the salt form may be adjusted depending on the clinical purpose between 20:80 and 80:20. The hyaluronic acid mixture with a higher ratio of LMWHA can be more helpful in speeding up the treatment; on the contrary, a higher ratio of HMWHA can provide a better degradation rate to prolong the treatment effect.

Another preferred embodiment of the present invention includes a hyaluronic acid mixture including LMWHA and HMWHA together with a steroid, immunosuppressive agent or other anti-inflammatory drug to potentiate the effect.

Another preferred embodiment of the present invention includes a hyaluronic acid mixture including both LMWHA and HMWHA constituting the major active ingredient with the proper excipient to formulate an oral solid dosage form (for example enteric coating), suppository (rectal suppository), perfusate fluid (for the rectum or the colon).

For oral formulation (for example enteric coated tablet), the enteric coating provides more resistance dissolution and digestion in the stomach, and after reaching intestine and colon, the enteric coating will be dissolved and the hyaluronic acid will be released to form a protection membrane at the inflammatory colon (the region uprising ascending colon or Transverse colon) in order to accelerate healing of the inflammatory region and also to prolong the treatment effect by long degradation rate.

For suppository or foam formulation, the suppository or foam containing above hyaluronic acid may be inserted into the anus and the hyaluronic acid will be released in the rectum and spread to other region of colon (for example the descending region) to form a protection membrane at the inflammatory colon in order to accelerate healing of the inflammatory region and also achieve sustained release effect.

For perfusion formulation (for example enema), the above hyaluronic acid mixture is the major active ingredient mixed with the excipient (for example but not limited to gelatin, collagen, chitosan, chondroitin, carbopol, agar, carboxymethyl cellulose (CMC) or phosphate buffered saline (PBS), at least one of the foresaid item or the compound of the foresaid items) directly used or in a soft tube to inject the above hyaluronic acid mixture into the colon. The hyaluronic acid mixture will be charged into the colon and spread to other region of colon (for example the descending region) to form a protection membrane at the inflammatory colon in order to accelerate the healing of the inflamed region and also achieve sustained release effect.

The preferred concentration of the hyaluronic acid mixture including LMWHA and HMWHA or pharmaceutically acceptable salt thereof ranges from 0.5 mg/ml to 5 mg/ml, but the preferred concentration in the solution form is within a range from 0.05% to 0.5% (w/v). The concentration is between 0.5 mg/ml to 50 mg/ml, and the preferred concentration is between 0.5 mg/ml to 5 mg/ml. The solution may be preferably formed in the concentration ranged from 0.05 to 5% (w/v); the more preferred solution formed in the concentration ranged from 0.05 to 0.5% (w/v). Furthermore, as for oral administration for prevention or improvement the preferred dose is at least 10 to 500 mg for each administration, and the pharmaceutically acceptable salt of the hyaluronic acid mixture is the sodium hyaluronan and the zinc hyaluronan.

Furthermore, the LMWHA in the Mw and the HMWHA in the Mw of the present invention can be applied accompanied with the steroid, immunosuppressive agent or anti inflammatory drug in order to achieve the better treatment effect.

The present invention is related to a method for treating and ameliorating a subject suffering from inflammatory bowel disease (IBD), comprising administering to the subject a therapeutically effective amount of a hyaluronic acid mixture including a low average molecular weight hyaluronic acid (LMWHA) and a high average molecule weight hyaluronic acid (HMWHA), wherein the LMWHA is in a range of 5 kilo to 1.5 million Da, and the Mw of HMWHA is in a range of 1.5 million to 5 million Da; and a mixing ratio of the LMWHA and the HMWHA is in a range from 20:80 to 80:20, wherein the concentration of the mixture of the LMWHA and the HMWHA is 0.5 mg/mL to 50 mg/mL. In a preferred embodiment, the molecule weight of the HMWHA is within a range of 1.5 million to 3.5 million Da. In a more preferred embodiment, the molecule weight of the HMWHA is 1.5 million Da to 2.5 million Da. In a preferred embodiment, the molecule weight of the LMWHA is 10 kilo Da to 1 million Da. In a more preferred embodiment, the molecule weight of the LMWHA is 100 kilo Da to 700 kilo Da. The preferred mixing ratio of the LMWHA and the HMWHA of the present invention is 1:1. The preferred concentration of the mixture of the LMWHA and the HMWHA of the present invention in a solution is 0.5 mg/mL to 5 mg/mL.

In a preferred embodiment, the hyaluronic acid mixture of the present i invention includes an excipient to formulate an oral solid dosage form, and the an excipient to formulate suppositories, foam, or a rectal perfusate or enema.

In a preferred embodiment, the hyaluronic acid mixture of the present invention is further combined with a steroid, immunosuppressive agent or anti-inflammatory drug.

In a more preferred embodiment, the hyaluronic acid mixture of the present invention is used to treat and prevent or ameliorate ulcerative colitis, acute enteritis, chronic enteritis or Crohn's disease and to aid in healing stomach and intestine wounds.

To prove the effect of the hyaluronic acid mixture in the present invention, the animal tests are performed under the professional laboratory and the results are presented as follows.

EXAMPLE

Example 1

1-1 Abstract

The purpose of the test is to evaluate the effect of the sample IBD98 in the animal body having the IBD. IBD98 was inserted into the rectum of the mice of the preventive group, then trinitrobenzenesulphonic acid (TNBS) was administered to induce the enteritis disease; followed up with continuous administration of the sample IBD98 through rectum for 3 days. Only administered the TNBS to the control group to induce the IBD. After 3 days of observation, all the mice were sacrificed on the $4^{th}$ day to inspect the clinical pathological changes, the index of blood sample before administrating the drug and after the termination of the test. The result indicates averages of the colonial inflammatory range of the preventive and control groups were 3.9 cm and 4.3 cm, which indicated no significant difference. The mice of the preventive and control groups have significant difference in the concentration of the TNF-$\alpha$ (Tumor Necrosis Factor-alfa) and IL-1$\beta$ (Interleukin-1$\beta$), indicating that the mice had the substantial induced inflammatory; the concentration of TNF-$\alpha$ of the preventive group after determination the test is significantly lower than the control group, and the difference is obvious. However, there was no significant difference in the concentration of IL-1$\beta$. The test has confirmed that such pattern can induce IBD in animal body and there is no significant difference in the clinical pathological change. Therefore, the effect on the sample can be evaluated by observing the recovering status after administrating the IBD98 sample. The test result indicates there is significant difference in the TNF-$\alpha$ in the preventive and control group performance. Therefore, the result proves that the IBD98 sample is substantially effective in reducing the inflammatory reaction in order to prevent the IBD.

1-2 Test Procedure:
  A. Test Purpose:
    to induce the IBD to the mice with the TNBS in order to evaluate the effect for treating or prevention of IBD or to reduce the inflammatory.
  B. Test Objective:
    IBD98, comprising LMWHA and HMWHA, and the HMWHA in a 2 million Da range and the LMWHA in a 1 million Da range, mixed in the ratio of 1:1, dissolved in PBS solution to produce a concentration of 0.5%.
  C. Method:
    1. Test Target:
      Selected 30 8-week old SPF grade Sprague Dawley male mice, and classified into two groups, each group containing 15 mice, and keep two mice in one cage set in the observation room of the laboratory.
    2. Animal Test:
      The mice were fasted for over 24 hours in the preventive group; test day 1, anesthetized the mice for administrating 1 ml of IBD98 via the rectum, and then administered 1 ml of TNBS (50 mg/mL) via the rectum; test day 2 to 4, administered 1 ml of IBD98 via the rectum; test day 5, sacrificed all mice to observe the colon for observing the clinical pathological changes.
      Fasted the mice for over 24 hours in the control group; test day 1, and then anesthetized the mice for administrating 1 ml of TNBS (50 mg/mL) via the rectum; test day 2 to 4, administered 1 ml of PBS via the rectum; test day 5, and then sacrificed all mice to observe the colon for observing the clinical pathological changes.
    3. Inflammatory Index Text
      Took the blood sample from the vein of the tail of the mice in both preventive and control groups on day 1 before starting the test, and then took blood sample from the heart after determination of the test; and collected the serum after centrifugation and inspected the serum for the changes of the TNF-α and IL-1β by ELISA (enzyme-linked immunosuppressant assay) respectively.

1-3 Test Figures:

CHART 1 clinical colonial pathological changes of the mice on the preventive group and the control group

| | preventive group | | | | control group | | |
|---|---|---|---|---|---|---|---|
| obj. no. | inflam. Range (cm) | ulcer lesion | grade | obj. no | inflam. Range (cm) | ulcer lesion | grade |
| A-2 | 2.5 | 1 | 2 | B1 | 2.5 | 0 | 2 |
| A-3 | 5 | 2 | 4 | B2 | 3.5 | 0 | 2 |
| A-4 | 4.5 | 1 | 3 | B3 | 4 | 1 | 3 |
| A-5 | 3.5 | 0 | 2 | B4 | 6 | 2 | 4 |
| A-6 | 4 | 1 | 3 | B5 | 5 | 2 | 4 |
| A-7 | 5.5 | 2 | 4 | B7 | 6 | 3 | 4 |
| A-8 | 4 | 1 | 3 | B8 | 4 | 1 | 3 |
| A-9 | 2.5 | 0 | 2 | B9 | 6 | 2 | 4 |
| A-10 | 4 | 1 | 3 | B11 | 1.5 | 0 | 1 |
| A-11 | 2 | 0 | 2 | B13 | 1.5 | 0 | 1 |
| A-13 | 6.5 | 2 | 4 | B14 | 6.5 | 3 | 4 |
| A-14 | 3 | 1 | 2 | B15 | 5 | 2 | 4 |
| A-15 | 4 | 1 | 3 | | | | |
| average | 3.9 | 1 | | | 4.3 | 1.3 | |

CHART 2 changes of the TNF-α and IL-1β in the serum of the mice before (D1) and 4 days after (D5) administration the drug to both the preventive

| | Preventive group | | | | | Control group | | | |
|---|---|---|---|---|---|---|---|---|---|
| Obj. no. | TNF-α (pg/mL) | | IL-1β (pg/mL) | | Obj. no. | TNF-α (pg/mL) | | IL-1β (pg/mL) | |
| | D1 | D5 | D1 | D1 | | D1 | D5 | D1 | D5 |
| A2 | 27.8 | 1933.7 | 0 | 869.6 | B1 | 14.3 | 586.5 | 1.0 | 42.1 |
| A3 | 28.6 | 847.8 | 29.6 | 94.8 | B2 | 23.1 | 2241.5 | 21.8 | 1325.2 |
| A4 | 22.2 | 110.3 | 0.7 | 44.8 | B3 | 26.6 | 1608.5 | 20.4 | 1680.1 |
| A5 | 12.8 | 481.9 | 0 | 130.3 | B4 | 22.2 | 1933.7 | 54.1 | 1229.8 |
| A6 | 25.6 | 1347.2 | 6.9 | 790.3 | B5 | 7.9 | 847.8 | 0 | 21.9 |
| A7 | 9.6 | 36.6 | 0 | 16.9 | B7 | 6.4 | 1068.5 | 0 | 29.4 |
| A8 | 18.7 | 458.7 | 0 | 39.1 | B8 | 15.4 | 2090.5 | 17.8 | 962.3 |
| A9 | 17.5 | 528.4 | 0 | 33.9 | B9 | 17.9 | 1498.2 | 0 | 46.9 |
| A10 | 16.3 | 1736.3 | 0 | 401.8 | B11 | 0.7 | 1387.9 | 22.3 | 197.5 |
| A11 | 10.3 | 331.0 | 0 | 11.3 | B13 | 1.0 | 714.2 | 23.4 | 25.0 |
| A13 | 30.1 | 1440.1 | 0 | 1069.8 | B14 | 0 | 1649.2 | 1.3 | 32.7 |
| A14 | 18.0 | 540.0 | 0 | 47.3 | B15 | 12.4 | 569.1 | 6.5 | 39.8 |
| A15 | 38.9 | 79.1 | 5.6 | 35.4 | | | | | |
| Ave. | 21.3 | 759.3** | 3.3 | 275.8* | Ave. | 12.3 | 1349.6**# | 14.1 | 469.4* |

**the concentration of the TNF-α in the serum of the preventive group mice in D5 and D1 has significant difference (P < 0.01), as well as the control group (P < 0.01).
*the concentration of the IL-1β in the serum of the preventive group mice in D5 and D1 has significant difference (P < 0.05), as well as the control group (P < 0.05).
the concentration of the TNF-α in the serum of the preventive group and control mice in D5 and D1 has significant difference (P < 0.05).

1.4 Test Result 30 mice were selected for performing the test and separate them into two groups as the preventive group and the control group, each group contains 15 mice and then fasted over 24 hours before running the test, and administering the enema for exhausting the faeces before administrating drug. Administered 1 mL of TNBS to the control group on Day 1 (D1) and administered PBS for the following 3 days (D2-D4); administered 1 mL of IBD98 to the preventive group on Day 1 (D1), and then administered 1 mL of TNBS after an hour, and then continued to administer IBD98 for the following 3 days (D2-D4). The mice of both groups on Day 5 (D5) were sacrificed for further performing dissection to inspect the intestinal lesion and the inflammatory range. The mice died during the test process are not accounted for the result of the test. There were 13 mice accountable in the preventive group and 12 in the control group at the end of the test. The average of the inflammatory range of the preventive group and the control group are respectively as 3.9 cm and 4.3 cm, which have insignificant difference (referring to chart 1).

The average concentration (pg/mL) of the inflammatory index TNF-$\alpha$ on D1 and D5 was observed to have risen from 21.3 to 759.3 in the preventive group and from 12.3 to 1349.6 in the control group, which indicates the significant difference ($P<0.01$); the average concentration (pg/mL) of the inflammatory index IL-1$\beta$ on D1 and D5 was observed to have risen from 3.3 to 275.8 in the preventive group and from 14.1 to 469.4 in the control group, which indicates the significant difference ($P<0.05$) as well. The indication shows that before inducing TNBS, the mice of the test substantially appeared the inflammatory reaction. Comparing the inflammatory index of the two groups after the continuous process of 3 days on Day 5, the average concentration of TNF-$\alpha$ is 759.3 in the preventive group, 1349.6 in the control group, there was a significant difference between these two groups ($P<0.05$); and the concentration of the TNF-$\alpha$ in the serum of the preventive group is substantially significantly lower than the control group. In other words, the mice treated with IBD98 had less inflammation than the untreated mice (referring to chart 2).

1-5 Conclusion

The IBD was induced in the both groups, in the following 3 days, the control group received no medical treatment and the preventive group was treated with the TNBS after treated with IBD98, the concentration of both TNF-$\alpha$ and IL-1$\beta$ of the inflammatory index in the two groups are substantially risen, which indicates the inflammatory relation was induced in the mice. The TNF-$\alpha$ concentration of the preventive group was significantly lower than the control group, which means there is a substantial effect for reducing the inflammatory reaction to the mice after treated with the IBD98.

Example 2

2-1 Abstract

IBD was induced in the tested animals is to evaluate the effect of the IBD98 among the animal body. TNBS was administered to the mice in the rectum to induce the intestinal lesion, and then the IBD98 sample was administered into the mice of the treating group and PBS (phosphate buffered saline) to the control group respectively via the rectum after 3 days. The mice were sacrificed after 7 days of the continuous treatment to inspect the clinical lesion. The result indicates the colonial inflammatory range is averagely about 1.25 cm in the treating group treated with the IBD98 sample, and 1.875 cm in the control group treated with PBS. There is 33% of the recovery comparing the treating group with the control group. In other words, the IBD in the mice treated with IBD98 is substantially advantageous for the recovery of the intestine tissue.

2-2 Test Procedure

A. Test Purpose:
to induce the IBD in the mice by administrating the TNBS and to evaluate whether IBD98 is advantageous for treating or preventing the IBD or reducing the inflammatory in the mice.

B. Test Object
IBD98, comprising LMWHA and HMWHA, and the HMWHA in a 2 million Da range and the LMWHA in a 1 million Da range, mixed in the ratio of 7:3, dissolved in PBS solution to obtain a concentration of 0.5%.

C. Method:
1. Test Target
   36 8-week old SPF grade Sprague Dawley male mice were selected and classified into two groups, each group containing 18 mice, and keeping two mice in one cage set in the observation room of the laboratory.
2. Animal Test
   The mice were fasted for over 24 hours; test day 1, and then anesthetized for administrating 1 mL of TNBS (tri-nitro-benzene sulphonic acid, 50 mg/mL) via the rectum, and then observed for 3 days, and picked out the mice with the soft stool or the diarrhea symptom on the third day.
   The mice of the treating group were anesthetized for administrating 1 mL of the IBD98 (5 mg/mL) on Day 4 to Day 10. The mice of the control group were anesthetized for administrating 1 mL of the PBS on Day 4 to Day 10, and then all the mice were sacrificed on Day 11 to observe the colon for observing the clinical lesion.

2-3 Test Figures:

CHART 1 the clinical intestinal lesion in the mice of the control group

| Obj. no | Inflam. Range (cm) | Ulcer lesion | Clinical grade |
|---|---|---|---|
| B-12 | 2.0 | 1 | 2 |
| B-13 | 2.5 | 0 | 2 |
| A-18 | 1.0 | 0 | 1 |
| B-18 | 0 | 0 | 0 |
| B-14 | 0.3 | 0 | 1 |
| B-15 | 2.0 | 0 | 1 |
| Average | 1.875 | 0.17 | — |

CHART 2 the clinical lesion and the corresponding recovery ratio of the mice in the treating group

| Obj. no | Inflame. range (cm) | Ulcer lesion | Clinical grade | Corresponding recovery ratio* |
|---|---|---|---|---|
| A-11 | 2.0 | 0 | 2 | 6.7 |
| A-15 | 1.5 | 0 | 1 | −20.0 |
| A-17 | 2.0 | 0 | 2 | 6.7 |
| A-3 | 1.5 | 0 | 1 | −20.0 |
| A-4 | 0.5 | 0 | 1 | −73.3 |

CHART 2-continued the clinical lesion and the corresponding recovery ratio of the mice in the treating group

| Obj. no | Inflame. range (cm) | Ulcer lesion | Clinical grade | Corresponding recovery ratio* |
|---|---|---|---|---|
| B-6 | 0.5 | 0 | 1 | −73.3 |
| A-13 | 2.0 | 0 | 1 | 6.7 |
| A-16 | 0.3 | 0 | 1 | −84.0 |
| B-4 | 1.0 | 0 | 1 | −46.7 |
| Average | 1.25 | 0 | — | −33.0 |

*Corresponding recovery ratio (%) = inflammatory range in the treating group − average of the inflammatory range in the control group/average of the inflammatory range in the treating group.

FIG. 1 shows the recovery (%) of the colonial lesion in the mice of the treating group comparing with control group.

2-4 Test Result:

36 mice were selected for performing the test and separated them into the treating group and the control group with 18 mice in each group. The mice were fasted for over 24 hours before the test. Enema was administered to exhaust the faeces and administer the TNBS before administrating drug. After observing for 3 days, two mice died and 5 confirmed with the IBD by the dissection. The mice with normal stool status were excluded, the mice with soft stool and diarrhea on Day 4 were considered. IBD98 was continued to be administered via the rectum of the 10 mice in the treating group and administered PBS to 7 mice in the control group for 7 days (D4 to D10). Each group lost one mouse during the test, and then all mice were sacrificed on Day 11 for inspecting the intestinal lesion and the inflammatory range.

In the control group, one mouse had no lesion, three mice had local inflammatory for 0.3 to 1 cm and grade 1 lesion, and two mice had local inflammatory for 2 to 2.5 cm and grade 2 lesion (referring to chart 1). In the treating group, 7 mice had local inflammatory for 0.3 to 1.5 cm and grade 1 lesion, and two mice had local inflammatory for 2 cm and grade 2 lesion (referring to chart 2). After statistical analysis, the average inflammatory range in the mice of the control group is 1.875 cm and 1.25 cm in the mice of the treating group; the recovery ratio of the treating group comparing with the control group is 33% (referring chart 2 and FIG. 1).

To prove the present invention, experiments about the degradation of the hyaluronic acid mixture in solution are performed and the results are as follows.

Example 3

The Degradation of HA in 1 U/ml HAase 3-1: Test Substance:

0.25 g high average molecule weight sodium hyaluronate powder (HMAHA; Mw: 2 MDa; Freda) and 0.25 g low average molecule weight sodium hyaluronate powder (LMAHA; Mw: 0.35 MDa; Freda) were added into 50 ml PBS buffer (Phosphate buffered saline) respectively to form 0.5% solution, and then stirred for 6 hours until the powder was totally dissolved, and then 0.05 g LMAHA powder and 0.2 g HMAHA powder (ratio 2:8; categorized as medium molecular weight sodium hyaluronate powder, MMAHA) were added into 50 ml PBS buffer, and then stirred for 6 hours until the powder was completely dissolved.

3-2 Test Solution:

Mobile phase solution of GPC (Gel permeation chromatography) system was prepared by: (1) adding 35.49 g $Na_2HPO_4$ powder into 450 ml deionized distilled water (dd water) and stirred for 30 minutes in room temperature to form 0.5 M $Na_2HPO_4$ solution; and (2) adding 18 g $NaH_2PO_4$ powder into 250 ml dd water and stirred for 30 minutes in room temperature to form 0.5 M $NaH_2PO_4$ solution.

3-3 Test Procedure:

1 U/ml HAase was prepared by dissolving HAase powder into PBS buffer at 4° C. 2 ml HA sample, 1 ml 10 U/ml HAase and 7 ml PBS buffer were mixed for 3 minutes by vortex in 15 ml glass tube. The tube was shaken by 50 rpm in water bath. 1 ml solution was taken after the 15, 30, 45, 60, 75, 90, 105, 120 minutes and then supplied with 1 ml HAase each time. Every 1 ml solution was filtered through 0.45 μm filter. 20 μl solution was injected into GPC system and then the diagram was recorded.

Figure 2:
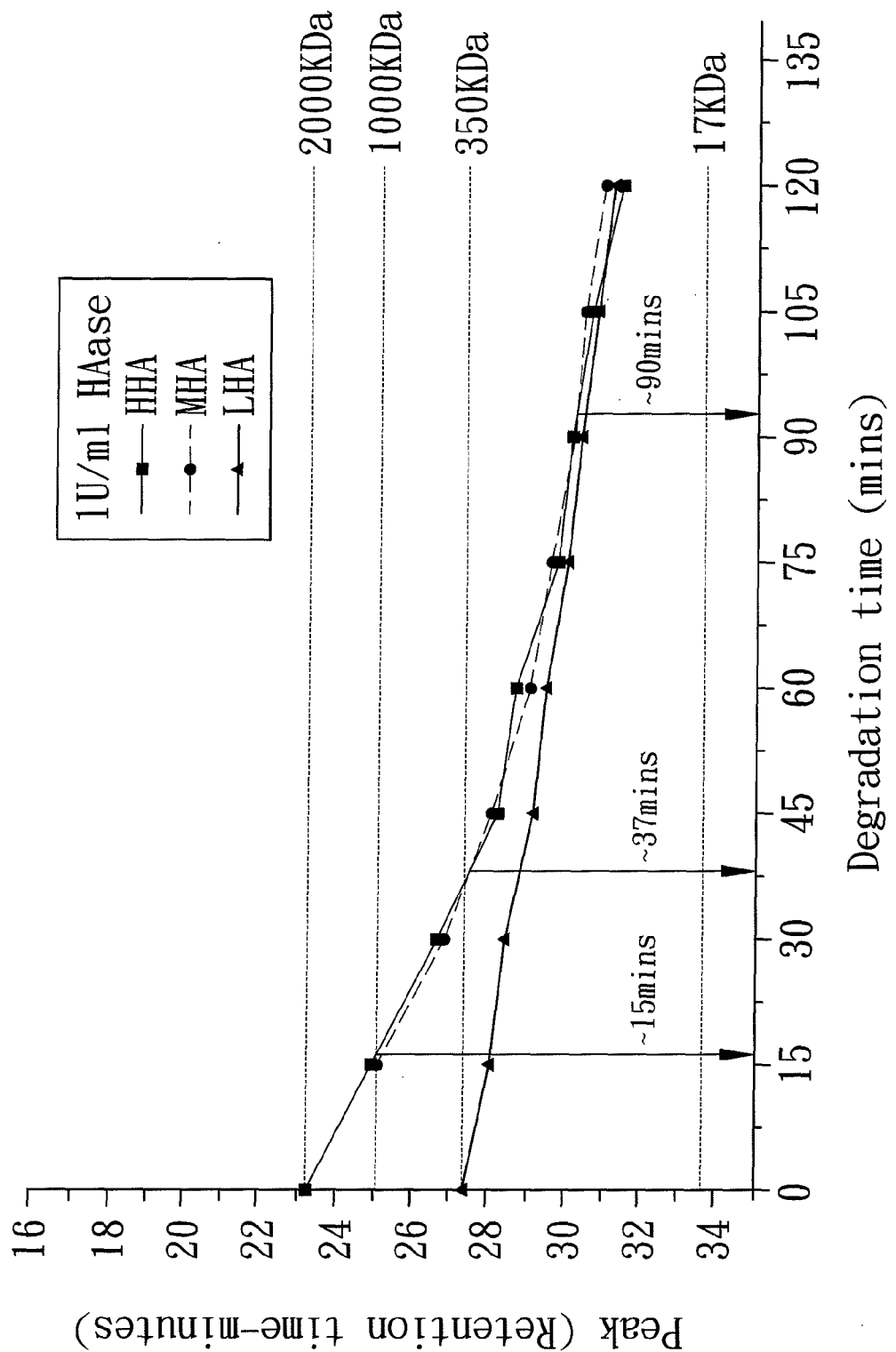
FIG. 2 illustrates degradation time of HAs and its flow rate in GPC subject to the effect of HAase in Example 3 in accordance with the present invention.

3-4 Test Data:

The situation of GPC system were (1) column: 2×GMP-Wxl (TSK-gel); (2) mobile phase flow rate: 1 ml/min; (3) temperature: 30° C. All values in the table were expressed as means of n observations. The histological index was analyzed by Student's t-test. FIG. 2 shows the retention time of HAs by GPC diagram.

3-5 Test Result:

The vertical axis represents the retention time in GPC, the horizontal axis represents the degradation time of HA in solution containing HAase. The horizontal dotted lines from up to down represent the retention time of 2 MDa, 1 MDa, 350 KDa and 17 KDa HAs, respectively. The retention time was obviously increased followed with the increased degradation of all three HAs. After 15 minutes of degradation, the average Mw of HMWHA and MMWHA were degraded to about 1 MDa. After 37 minutes of degradation, the average Mw of HMWHA and MMWHA were degraded to about 350 KDa. After 90 minutes of degradation, the average molecular weights of HMWHA, MMWHA and LMWHA were degraded such that no obvious difference exists among the average molecular weights, which were all larger than 17 KDa.

3-6: Conclusion:

HAase was used to cause degradation of hyaluronic acids. Subject to the characteristics of high flow rate of large molecular weight substances and low flow rate of small molecular weight substances in GPC, the retention time of large molecular weight substances and small molecular weight substances were measured. With increase in degradation time to make the molecular weight smaller, the flow rate was relatively increased. Thereby, experiments show that Mw of HMWHA will gradually become Mw of LMWHA through degradation.

Example 4

The Degradation of HA in 0.1 N HCl 4-1 Test Substance: Same as Example 3.

4-2 Test Solution: Same as Example 3.

4-3 Test Procedure:

Artificial gastric juice (0.1 N HCl) was prepared by mixing 5.72 ml 17.5 N HCl and 90 ml dd water and stirred for 10 minutes as a stocking solution. 2 ml of HMWHA, MMWHA and LMWHA were mixed with 8 ml artificial gastric juice, respectively in a 15 ml glass tube and by vortex for 3 minutes. The tube was shaken by 50 rpm in 37° C. water bath. 1 ml solution was taken after the 6, 12, 24, 48 hours and then supplied with 1 ml artificial gastric juice each time. Every 1 ml solution was filtered through 0.45 μm filter. 20 μl solution was injected into GPC system and then the diagram was recorded.

Figure 3:
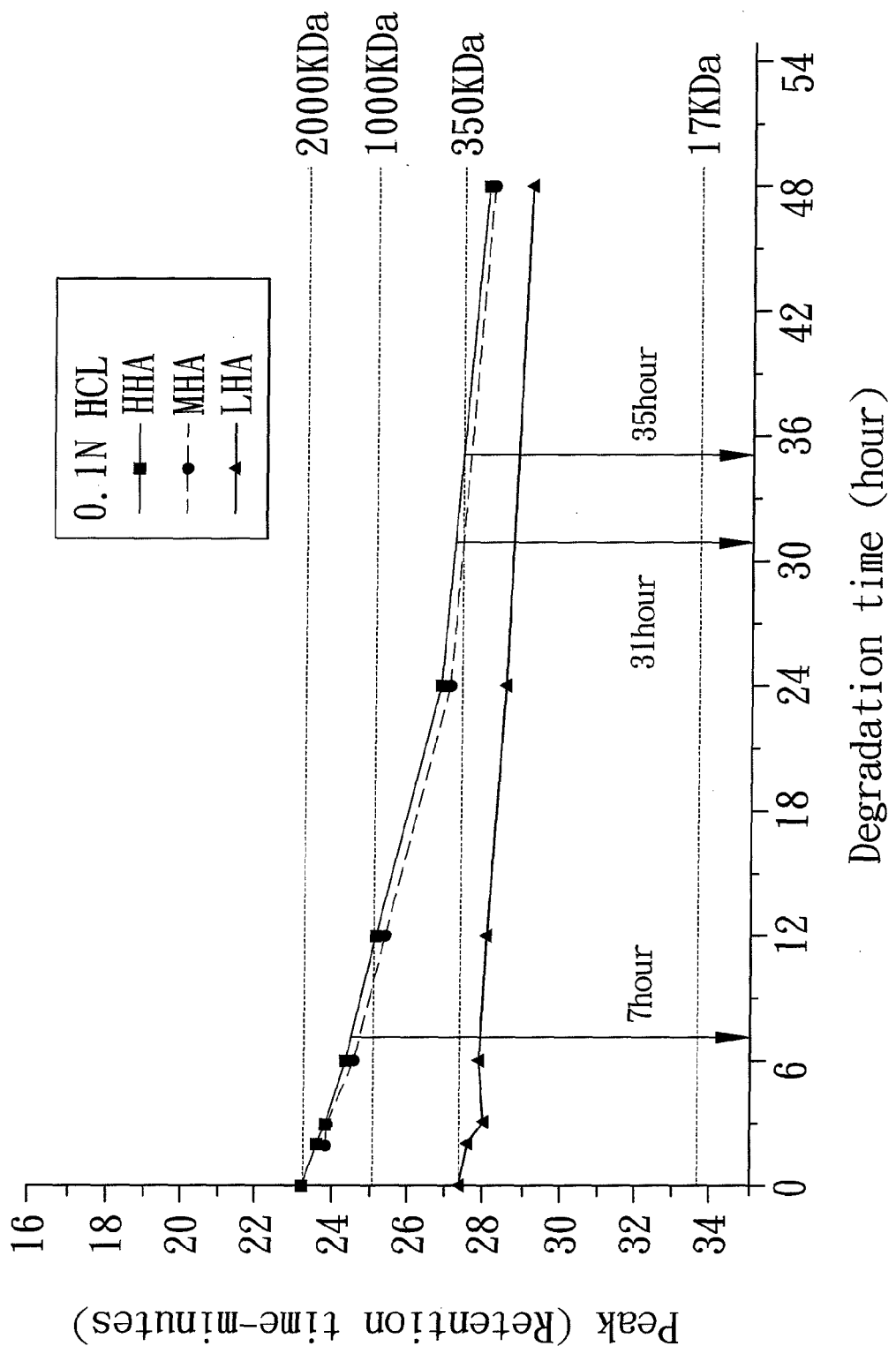
FIG. 3 illustrates degradation time of HAs and its flow rate in GPC, subject to the effect of 0.1N HCl in Example 4 in accordance with the present invention.

4-4 Test Data:
All values in the table were expressed as means of n observations. The histological index was analyzed by Student's t-test. FIG. 3 shows the retention time of HAs in GPC diagram.

4-5 Test Result:
The vertical axis represents the retention time in GPC, the horizontal axis represents the degradation time of HA in artificial gastric juice. The horizontal dotted lines from up to down represent the retention time of 2 MDa, 1 MDa, 350 KDa and 17 KDa HAs, respectively. The retention time was slowly increased followed by the increased degradation of all three HAs. After 7 hours of degradation, the average molecular weights of HMWHA and MMWHA were degraded to about 1 MDa. After 31 hours of degradation, the average Mw of MMWHA was degraded to about 350 KDa. After 35 hours of degradation, the average Mw of HMWHA was degraded to about 350 KDa. The aforementioned data all indicate that HA was slowly degraded in the artificial gastric juice whereas the average molecular weights of HMWHA and MMWHA were larger than 1 MDa after 6 hours of degradation, and the average molecular weights of HMWHA and MMWHA were larger than 350 KDa after 24 hours of degradation.

4-6 Conclusion:
In the aforesaid experiment, artificial gastric juice (0.1 N HCl) was employed to simulate the human stomach environment and pH to let hyaluronic acids degrade. Subject to the characteristics of high flow rate of large molecular weight substances and low flow rate of small molecular weight substances in GPC, the retention time of large molecular weight substances and small molecular weight substances were measured. With increase in degradation time to make the molecular weight smaller, the flow rate was relatively increased. Thereby, experiments show that HMWHA will gradually become LMWHA through degradation.

Example 5

The Adhesion of HA in Colon Tissue (IVIS Image System-vision 3)

5-1 Test Substance:
LHA and HHA were prepared as the same as Example 3. MMWHA (MMWHA; Mw: 1 MDa; Freda) were added into 50 ml PBS buffer, and then stirred for 6 hours until the powder was totally dissolved and ready for use in the following steps. Fluorescent HA (HA-0 was prepared by (1) 0.39 g MES free acid (2-(N-morpholino) ethanesulfonic acid, Calbiochem) and was dissolved in 100 ml dd water. (2) Solution A: 65 mg fluororesceinamine powder, (isomer I, Fluka) was dissolved in 9 ml 95% EtOH solution and then stirred for 10 minutes under a condition that light was prohibited. (3) Solution B: 359 mg EDC powder (N-(3-Dimethylamino propyl)-N-ethyl carbodiimide hydrochloride, Sigma) was dissolved in 9 ml MES buffer and then stirred for 10 minutes. (4) Solution C: 216 mg NHS powder (N-Hydroxysuccinimde, Sigma) was dissolved in 9 ml MES buffer and then stirred for 10 minutes. (5) 3 ml Solution A was slowly dropped into 50 ml 0.5% HA solution and then stirred for 10 minutes under a condition that light was prohibited. (6) 3 ml Solution B and 5 ml Solution C were separately dropped into the solution of step (5) and then stirred for 10 minutes under a condition that light was prohibited. (7) 0.02 M MES buffer was slowly added into the solution of step (6) until the volume reached 100 ml and then stirred for 24 hours at room temperature under a condition that light was prohibited. (8) The product after reaction was poured into a dialysis tubing (MW: 12000~14000) in 5 L dd water as a dialysis solution and then stirred for 5 days at 4° C. under a condition that light was prohibited with dialysis solution being changed every 12 hours until the dialysis solution had no fluorescence. (9) The liquid after dialysis was allocated into 50 c.c. plastic centrifuge tubes and then reserved at −20° C. refrigerator overnight followed by drying in a freeze-drying machine under a condition that light was prohibited. (10) The dried HA-f powder was reserved at −20° C. refrigerator. (11) 50 mg HA-f powder was slowly added into 10 ml PBS buffer and then stirred for 6 hours until the powder was completely dissolved.

5-2 Test Tissue:
Colon tissue of SD-rat (Sprague-Dawley Rat) aged 7-8 weeks was cut by scalpel and then washed by PBS buffer followed by being cut to 3-4 cm long with soaking in PBS buffer finally.

5-3 Test Procedure
Injured colon tissue was prepared by brushing by toothbrush for 20 times longitudinally and then soaking in PBS buffer. Normal and injured colon tissues were put into a 12-well plate and then 1 ml 0.5 HA-f solution was added into each well and shaken for 2 hours at room temperature. Surplus HA-f solution was sucked by tip 2 hours later, and then soaked into PBS buffer for 10 minutes followed by removing PBS buffer repeatedly for 3 times. Cleaned colon tissue was placed in a 12-well plate with lining tissue upwards and then placed onto the dock of the IVIS (in vivo image system, XENOGEN). The default parameter was set up as GFP (green fluorescent protein) whereas the excitation was 465 nm and the emission was 500 nm and then the image was captured by software.

Figure 4:
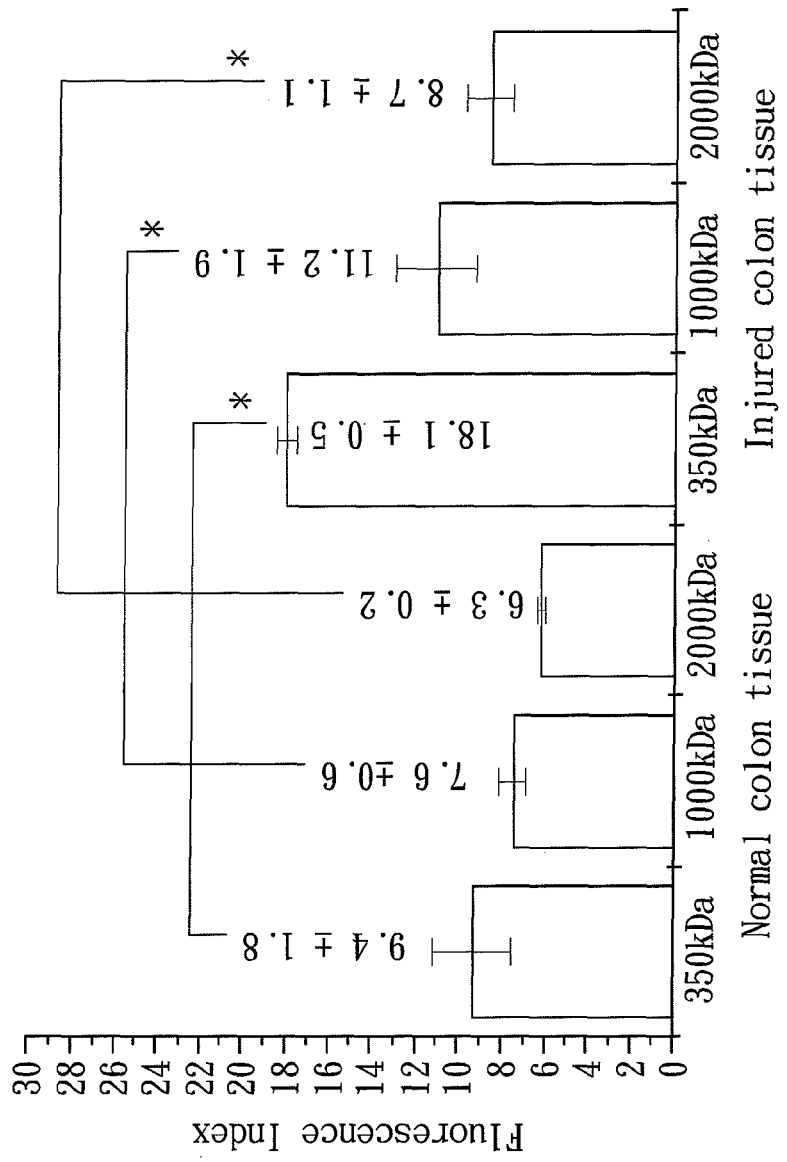
FIG. 4 illustrates fluorescent index of the normal colon tissue and injured colon tissue with fluorescent HA in Example 5 in accordance with the present invention.

5-4 Test Data:
All values in the table are expressed as means of n observations. The histological index was analyzed by Student's t-test. The fluorescent index was quantified and arranged as in FIG. 4.

5-5 Test Result:
The fluorescent index of normal colon tissue was defined as 1. The other colon tissues tests were calibrated by the defined value. The result showed that the HAs with the same average Mw were absorbed in the injured colon tissues obviously higher than in the normal colon tissues ($P<0.01$). In comparing the difference between HAs of three different average molecular weights absorbed in the injured colon tissues, the fluorescent index of absorption of 350 KDa HA by the injured colon tissues was obviously higher than that of HAs of the other two average molecular weights (2 MDa and 1 MDa). Further, the fluorescent index of absorption of 1 MDa HA by even normal or injured colon tissues was higher than 2 MDa HA.

5-6 Conclusion:
Fluorescent hyaluronic acids were prepared, and then different molecular weights of fluorescent hyaluronic acids were placed in normal and injured colon tissues, and then respective fluorescent indexes were measured using IVIS. Subject to the fluorescent indexes, the effect of absorption was known. The result showed that injured colon tissue had better absorption on hyaluronic acids; lower average molecule weight (Mw of LMWHA) had better absorption than higher average molecule weight (Mw of HMWHA).

Example 6

The Body Weight Change of Rat with or without Administration of HA Aimed at Colitis 6-1 Test Purpose:
To induce the colitis in the SPF grade SD (Sprague-Dawley) rats with the TNBS in order to evaluate the effect for treating or preventing colitis by two kinds of mixing HAs differing in weight proportion.

6-2. Test Objective:
IBD98, comprising LMWHA and HMWHA, whereas the HMWHA was 2 million Da and the LMWHA was 350 kilo Da, mixed in the ratio of 8:2 and 1:1 by weight which were categorized into group A and group B, respectively, and dissolved in PBS solution to produce a concentration of 0.125% (w/v).

6-3. Test Method:
A. Test Target:
Rats aged 8 weeks were selected, and classified into three groups: group A represented mixing ratio of 8:2; group B represented mixing ratio of 1:1; group C was treated by PBS instead of HA.

B. Animal Test:
All rats of the treating group were fasted for 2 days; in test day 1, the rats were anesthetized for administrating 1 ml of TNBS (50 mg/mL) via the rectum; through test days 4 to 14, administering 1 ml of two categories of IBD98 via the rectum in groups A and B; in test day 9, the body weight changes of half rats in groups A and B were observed. And the body weight changes of the other half rats were observed in day 14. All rats of the control group were fasted for 2 days; in test day 1, the rats were anesthetized for administrating 1 ml of TNBS (50 mg/mL) via the rectum; in test days 4 to 14, administering 1 ml of PBS via the rectum; in test day 9, the body weight changes of half rats in group C were observed. And the body weight changes of the other half rats were observed in day 14.

Figure 5:
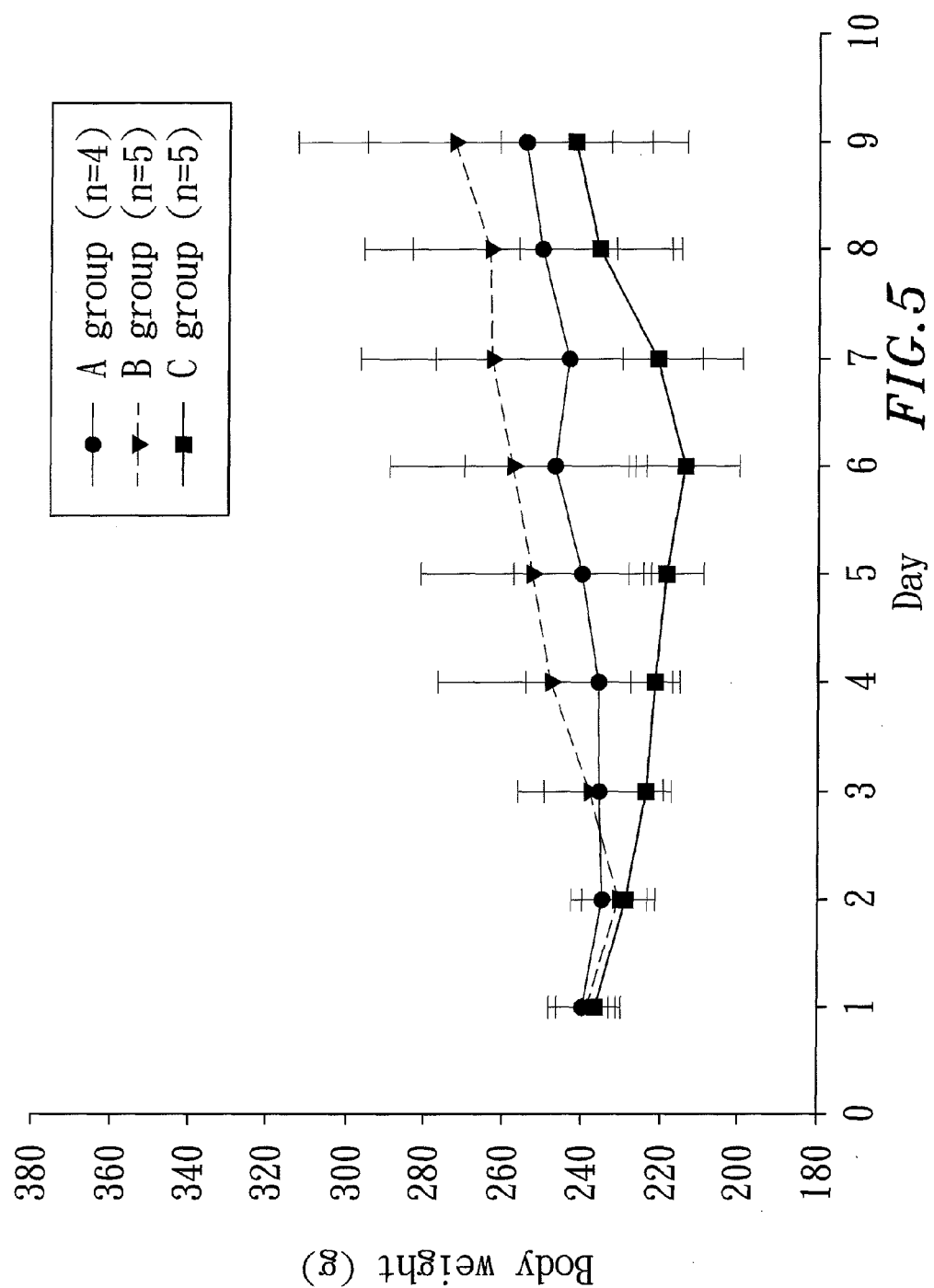
FIG. 5 illustrates the change of average body weight in each group of rats from day 1 to day 9 in Example 6 in accordance with the present invention.
Figure 6:
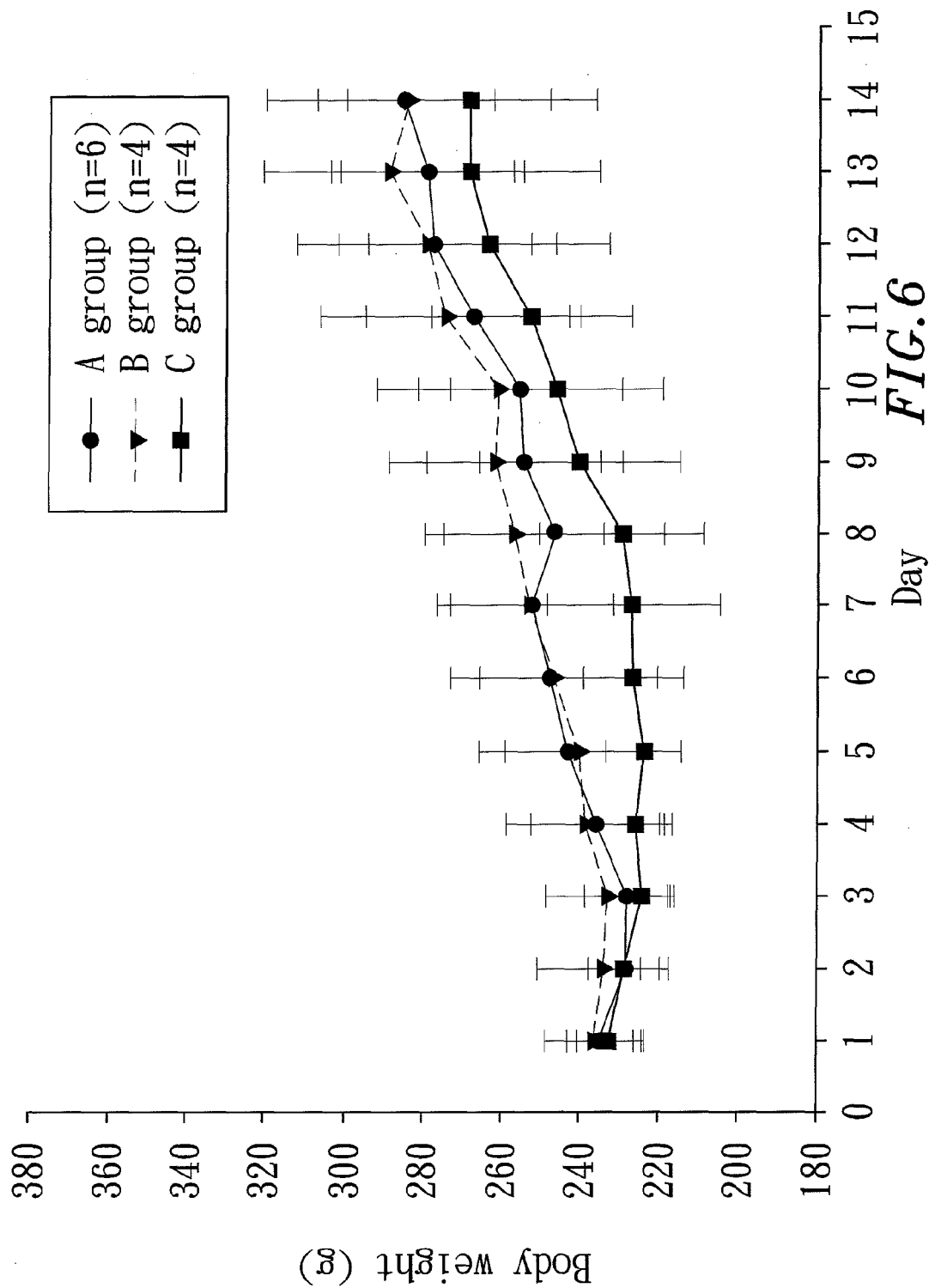
FIG. 6 illustrates the change of average body weight in each group of rats from day 1 to day 14 in Example 6 in accordance with the present invention.

6-4 Test Data:
The trend showed groups A and B both had relief effects on colitis which also represented IBD through day 1 to day 14 (FIGS. 5 and 6).

6-5 Conclusion:
Inflammatory index: the present invention used changes of average body weight as an index to view the amelioration of colitis (IBD). The change of the body weight is a convenient and direct index to check the treatment result. The trend showed groups A and B both had relief effects on colitis which also represented IBD through day 1 to day 14 (FIGS. 5 and 6). In average weight changes between control and HAs, treatment effect of colitis caused the average body weights of group with administered HAs to be kept higher than those of control group during the whole experimental period even till test day 14 (FIG. 6).

In conclusion, the present invention provides a method for treating and preventing inflammatory bowel disease (IBD) by applying a predetermined therapeutically effective amount of a mixture of hyaluronic acid to individuals, wherein the hyaluronic acid mixture comprises at least two pharmaceutically acceptable hyaluronic acid in the salt form with various Mw (molecular weight), and the various degradation rates among various Mw enables the LMWHA with low Mw to spread rapidly to the HMWHA with higher Mw to accordingly maintain the degradation for better subtend release effect, thus to achieve the goal of prompt treatment and retarding effect.

While the invention has been described in conjunction with a specific best mode, it is to be understood that many alternatives, modifications, and variations will be apparent to those skilled in the art in light of the foregoing description. Accordingly, it is intended to embrace all such alternatives, modifications, and variations in which fall within the spirit and scope of the included claims. All matters set forth herein or shown in the accompanying drawings are to be interpreted in an illustrative and non-limiting sense.

What is claimed is:

1. A method for treating and ameliorating a subject suffering from inflammatory bowel disease (IBD), comprising administering to the subject a therapeutically effective amount of a hyaluronic acid mixture,
wherein said mixture consists essentially of a low average molecular weight hyaluronic acid (LMWHA) and a high average molecule weight hyaluronic acid (HMWHA), wherein said average MW of said LMWHA is 100 kilo Da to 700 kilo Da, and said average MW of said HMWHA is 1.5 million Da to 2.5 million Da, and a mixing ratio of said LMWHA and said HMWHA is in a range from 20:80 to 80:20, wherein the concentration of the mixture of said LMWHA and said HMWHA is 0.5 mg/ml to 50 mg/ml.

2. The method of claim 1, wherein said mixing ratio of said LMWHA and said HMWHA is 1:1.

3. The method of claim 1, wherein the concentration of the mixture of said LMWHA and said HMWHA in a solution is 0.5 mg/ml to 5 mg/ml.

4. The method of claim 1, wherein said hyaluronic acid mixture includes an excipient to formulate an oral solid dosage form.

5. The method of claim 1, wherein said hyaluronic acid mixture includes an excipient to formulate suppositories, foam, or a rectal perfusate or enema.

6. The method of claim 1, wherein said hyaluronic acid mixture is further combined with a steroid, immunosuppressive agent or anti-inflammatory drug.

7. The method of claim 1, wherein said hyaluronic acid mixture is used to treat ulcerative colitis, acute enteritis, chronic enteritis or Crohn's disease and to aid in healing stomach and intestine wounds.

* * * * *